United States Patent [19]

Brown et al.

[11] Patent Number: 5,420,135
[45] Date of Patent: May 30, 1995

[54] SUBSTITUTED QUINOLINE DERIVATIVES

[75] Inventors: Thomas H. Brown, Harlow; Robert J. Ife, Welwyn; Colin A. Leach, Welwyn; David J. Keeling, Welwyn, all of England

[73] Assignee: Smith Kline & French Laboratories Limited, Welwyn Garden City, England

[21] Appl. No.: 783,101

[22] Filed: Dec. 10, 1990

[30] Foreign Application Priority Data

Dec. 14, 1989 [GB] United Kingdom ............... 8928281

[51] Int. Cl.$^6$ ............................................ A61K 31/44
[52] U.S. Cl. .................................................. 514/293
[58] Field of Search ..................... 546/82, 83; 514/293

[56] References Cited

U.S. PATENT DOCUMENTS 4,689,338 8/1987 Gerster ............................. 514/293

OTHER PUBLICATIONS

T. Brown et al., J. Med. Chem. 1990, 33, 527–533.

Primary Examiner—Raymond Henley, III
Assistant Examiner—Phyllis G. Spivack
Attorney, Agent, or Firm—Linda E. Hall; Stuart R. Suter; Edward T. Lentz

[57] ABSTRACT

Substituted quinoline derivatives are described as inhibitors bone resorption with in particular, the compound 1-(2-methylphenyl)imidazo[4,5-c]quinoline hydrochloride.

6 Claims, No Drawings

SUBSTITUTED QUINOLINE DERIVATIVES

The present invention relates to substituted quinoline derivatives, processes for their preparation, intermediates useful in their preparation, pharmaceutical compositions containing them and their use in therapy.

Substituted quinoline derivatives are known in the art. For example, in J. Chem. Soc. 1957, 3448, J. Pharm. Soc. Japan 1961, 18, 363, 1961 and 479, certain 1-(substituted phenyl)-4-methyl-2,3-dihydropyrrolo[3,2-c]quinolines, 1-phenyl-4-halo-2,3-dihydropyrrolo[3,2-c]quinolines and 1-phenyl-2,3-dihydropyrrolo[3,2-c]quinolines are disclosed as synthetic intermediates but no therapeutic activity is disclosed for such compounds. In addition, J. Pharm. Soc. Japan 1957, 77, 85, and ibid. 1961, 90, disclose certain 1-(substituted phenyl)-4-methyl-2,3-dihydropyrrolo[3,2-c]quinolines and report antibacterial activity for the compounds but do not disclose formulations containing said compounds or information concerning a specific therapeutic utility for the compounds. Finally, EP-A1-0307078 discloses certain 2,3-dihydropyrrolo[3,2-c]quinolines as inhibitors of the $H^+K^+ATPase$ enzyme and their use as anti-ulcer agents.

It has now been found that certain heterocyclic [4,5-c]quinolines also have activity as inhibitors of the $H^+K^+ATPase$ enzyme, and in addition are inhibitors of bone-resorption, and are expected to have utility in the treatment of diseases such as, for example osteoporosis and Paget's disease.

Accordingly the present invention provides, in a first aspect compounds of structure (I)

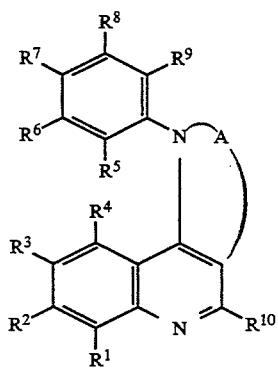

(I)

in which $R^1$ to $R^4$ are the same or different and are each hydrogen, $C_{1-4}$alkyl, $C_{1-6}$alkoxy, phenyl, $C_{1-6}$alkylthio, $C_{1-4}$alkanoyl, amino, $C_{1-6}$alkylamino, di$C_{1-6}$alkylamino, halogen, trifluoromethyl or nitro, provided that at least two of $R^1$ to $R^4$ are hydrogen.

$R^5$ to $R^9$ are the same or different and are each hydrogen, $C_{1-6}$alkyl, $C_{1-6}$alkoxy, $C_{1-6}$alkylthio, halogen, cyano, amino, hydroxy, carbamoyl, carboxy, $C_{1-6}$alkanoyl, trifluoromethyl or nitro, provided that at least two of $R^5$ to $R^9$ are hydrogen;

$R^{10}$ is hydrogen, $C_{1-6}$alkyl, $C_{1-6}$alkoxy, halogen, hydroxy, —$CH_2OH$, $C_{1-6}$alkylthio, $NH(CH_2)_nOH$ in which n is 0 to 4 or a group —$NR^{11}R^{12}$ in which $R^{11}$ and $R^{12}$ are the same or different and are each hydrogen or $C_{1-6}$alkyl or together with the nitrogen atom to which they are attached form a saturated or unsaturated ring; and A is $$-N=N-; \quad -\overset{O}{\underset{\|}{C}}S-, \quad or \quad -CH=N-;$$

and pharmaceutically acceptable salts thereof.

Suitably A is A is $$-\overset{O}{\underset{\|}{C}}S-, \quad or \quad -CH=N-;$$

preferably A is —N=N—.

Suitably, $R^1$ to $R^4$ are all hydrogen; more suitably only two of $R^1$ to $R^4$ are hydrogen. Preferably three of $R^1$ to $R^4$ are hydrogen. More preferably $R^2$ to $R^4$ are hydrogen and $R^1$ is other than hydrogen. Most preferably $R^2$ to $R^4$ are hydrogen and $R^1$ is $C_{1-6}$alkyl or $C_{1-6}$alkoxy.

Suitably $R^5$ to $R^9$ are all hydrogen. Preferably three of $R^5$ to $R^9$ are hydrogen. More preferably $R^5$ to $R^8$ are all hydrogen and $R^9$ is other than hydrogen. Most preferably $R^5$ to $R^8$ are all hydrogen and $R^9$ is $C_{1-6}$alkyl, in particular, methyl.

Suitably $R^{10}$ is halogen or $C_{1-6}$alkylthio. Preferably $R^{10}$ is hydrogen, or a group $NR^{11}R^{12}$.

Suitably $R^{11}$ and $R^{12}$ together with the nitrogen atom to which they are attached form a saturated or unsaturated ring. Preferably $R^{11}$ and $R^{12}$ are the same or different and are each hydrogen or $C_{1-6}$alkyl.

$C_{1-6}$alkyl groups (either alone or as part of another group) can be straight or branched.

It will be appreciated that compounds of structure (I) in which one or more of $R^1$ to $R^{10}$ is a $C_{3-6}$alkyl group (either alone or as part of another group) may contain an assymetric centre due to the presence of the $C_{3-6}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

The compounds of the present invention can be prepared by processes analogous to those known in the art. The present invention therefore provides in a further aspect a process for the preparation of a compound of structure (I) or a pharmaceutically acceptable salt thereof which comprises (a) cyclisation of a compound of structure

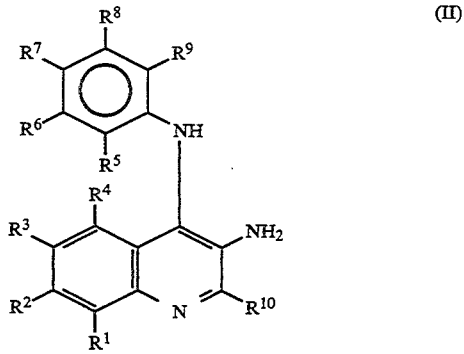

(II)

in which $R^1$ to $R^{10}$ are as described for structure (I) with formic acid, sodium nitrite/hydrochloric acid or carbon disulphide in the presence of a base to form a compound of structure (I) in which A is

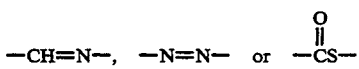

respectively;

(b) for compounds in which $R^{10}$ is other than $C_{1-6}$alkyl reaction of a compound of structure (IV)

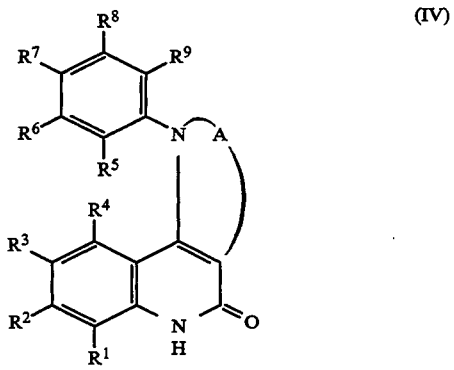

in which $R^1$ to $R^9$ and A are as described for structure (I) with a reagent providing the group $R^{10}$, and optionally therafter
converting one group $R^{10}$ into another group $R^{10}$; forming a pharmaceutically acceptable salt.

Suitably the cyclisation of a compound of structure (II) is carried out in the presence of a suitable reagent which provides for the formation of the heteroyclic ring A. For example, when A is —CH=N—, the cyclisation is carried out in formic acid at reflux temperature until reaction is complete; when A is —N=N—, the cyclisation is carried out in an aqueous solution of sodium nitrite and hydrochloric acid at ambient temperature, and when A is

the cyclisation is carried out in the presence of carbon disulphide acid a suitable base, such as triethylamine in ethanol, at a temperature of about 40°-60°. Other suitable conditions for these reactions will be apparent to those skilled in the art.

Suitable reagents providing the group $R^{10}$ for structure (IV) will be apparent to those skilled in the art and will of course depend on the nature of the group $R^{10}$ sought. For example in the preparation of compounds of structure (I) in which $R^{10}$ is halogen, for example chlorine, a suitable compound of structure (IV) can be reacted with phosphorous oxychloride, optionally in the presence of a suitable solvent and at an appropriate temperature; for compounds of structure (I) in which $R^{10}$ is $NH_2$, a suitable compound of structure (IV) can be reacted with phenyl phosphorodiamidate, again optionally in the presence of a suitable solvent at an appropriate temperature.

Alternatively, compounds of structure (I) can be prepared from other compounds of structure (I), for example, compounds of structure (I) in which $R^{10}$ is halogen can be converted into compounds of structure (I) in which $R^{10}$ is other than halogen by reaction with an appropriate nucleophilic reagent capable of displacing the chlorine atom for example as described in EP-A1-307078.

Pharmaceutically acceptable acid addition salts of the compounds of structure (I) can be prepared by standard procedures by, for example, reaction with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as, for example, citric, maleic or fumaric acids.

The intermediate compounds of structure (II) can be prepared by procedures known in the art, for example, by reduction of the corresponding 3-nitro compound, which itself can be prepared from 4-chloro-3-nitroquinoline (J. Med. Chem. 1974, 17, 245) and 2-methylaniline (commercially available).

The Compounds of structure (I) and their pharmaceutically acceptable salts exert an anti-secretory effect by inhibition of the gastrointestinal H+K+ATPase enzyme (Fellenius E., Berglindh T., Sachs G., Olke L., Elander B., Sjostrand S. E., and Wahlmark B., 1981, Nature, 290, 159–61).

The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, and Zollinger-Ellison Syndrome.

Further, the compounds of structure (I) can be used in the treatment of other disorders where an anti-secretory effect is desirable for example in patients with gastritis, NSAID induced gastritis, gastric ulcers, acute upper intestinal bleeding, in patients with a history of chronic and excessive alcohol consumption, and in patients with gastro oesophageal reflux disease (GERD).

In addition to the anti-ulcer properties the compounds of structure (I) are of use in medicine as inhibitors of bone resorption. In normal subjects where is a balance between bone resorption and bone formation, however, in subjects with bone affected diseases such as osteoporosis, Paget's disease and hyperparathyroidism and related disorders this balance is disturbed. As a consequence of this imbalance the subject suffers a loss of bone tissue, decreased bone mass and bone fragility which can result in fracturing of bones. Bone resorption (or bone loss) is associated with the activity of osteoclast cells, and it is thought that agents which inhibit the activity of such cells (and so inhibit bone resportion) will have a beneficial effect on the reduction of bone loss and be of benefit in the treatment of the above-noted disease states. The present compounds have been found to be inhibitors of osteoclast activity and bone resorption and are expected to be of use in medicine in the treatment of diseases in which bone loss is a factor, in particular osteoporosis, Paget's disease and hyperporathyroidism.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of structure (I) or a pharmaceutically acceptable salt thereof calculated as the free base.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of structure (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

The following examples illustrate the invention. Temperatures are recorded in degrees centigrade.

Preparation 1

4 - (2 -Methylphenylamino)-3 -nitroquinoline

4-Chloro-3-nitroquinoline (J. Med. Chem. 1974, 17, 245) (2.08 g, 0.01 mol) and 2-methylaniline (2.14 g, 0.02 mol) were dissolved in THF (50 ml) and the mixture stirred at reflux for 16 hours, during which time a pale yellow solid was deposited. After cooling, the solvent was evaporated and the residue dissolved in 2M HCl (80 ml). The acidic solution was extracted with $CHCl_3$ ($\times 3$) and the chloroform solution washed with aqueous $NaHCO_3$ and water. Drying and evaporation of the chloroform gave an orange-yellow solid which was crystallised from absolute ethanol to give the title compound (1.2 g, 43%) as orange needles, m.p. 137°–138°.

Preparation 2

3-Amino4-(2-methylphenylamino)quinoline 4-(2-methylphenylammino)-3-nitroquinoline from preparation 1 (5.2 g, 18.6 mmol) was dissolved in ethylacetate (250 ml) and stannous chloride (20.9 g, 93 mmol) added. The mixture was stirred at room temperature for two hours, filtered through celite and the solvent evaporated to give a solid residue. This was triturated with $CHCl_3$, filtered and dissolved in water. The aqueous solution was basified with NaOH (to pH 12) and extracted with chloroform. The organic extracts were combined, washed with water, dried and evaporated to a yellow solid which was recrystallised several times from ethanol/petroleum ether to give the title compound as the base, mp 156°–158° . A portion of this base (0.47 g) was treated with ethanolic HCl (30 ml), filtered and the solution evaporated. Recrystallisation from ethanol/ether gave a pale yellow solid (0.43 g), m.p. 303°–305°.

Example 1

1-(2-Methylphenyl)imidazo[4,5,-c]quinoline hydrochloride

3-Amino-4-(2-methylphenylamino)quinoline (0.9 g, 3.6 mol) and formic acid (10 ml) were mixed at room temperature then stirred at reflux for 3 hours, cooled and evaporated to dryness. The residual oil was partitioned between water and $CCCl_3$, the chloroform solution washed with aqueous $NaHCO_3$ and water, then dried and evaporated to give a dark viscous oil. (0.85 g). This was dissolved in ethanolic HCl (50 ml) and the solution evaporated to dryness. Recrystallisation from ethanol/ether gave the title compound as a white solid (0.55 g, 59%), m.p. 266°–270°.

Example 2

1-(2-Methylphenyl)triazolo[4,5-c]quinoline

A solution of sodium nitrite (0.82 g, 12 mmol) in water (10 ml) was added dropwise to a stirred suspension of 3-amino-4-(2-methylphenylamino)quinoline (2.0 g,8 mmol) in 2M HCl (80 ml) at 0.5°. The solid gradually dissolved to give a pale orange solution which deposited a solid after about 1 hour. After warming to room temperature the solid was collected, washed with water and recrystallised from aqueous ethanol with charcoaling, to give the title compound as a white solid (0.55 g, 26%), m.p. 140°–142°.

Example 3

1-{2-Methylphenyl)-2(3H)-thioimidazo[4,5-c]quinolone

3-Amino-4-(2-methylphenylamino)quinoline (2.3 g, 9.23 mmol) was mixed with $CS_2$ (10 ml), triethylamine (2 ml) and EtOH (60 ml). The solution was warmed at 42° (oil-bath temperature) for 16 hours, during which time a solid was deposited. The solid was collected (1.4 g) and recrystallised from aqueous ethanol to give the title compound as a white solid, m.p. 288°–290°.

Biological Data (1) H+K+ATPase Activity

The effects of a single high concentration (100 μM) of a compound of structure (I) on K-stimulated ATPase activity in lyophilised gastric vesicles was determined. Preferred compounds of structure (I) were also tested over a range of concentrations to determine $IC_{50}$ values.
(i) Preparation of lyophilised gastric vesicles (H/K-ATPase).

Lyophilised gastric vesicles were prepared from pig fundic mucosa after the method of Keeling st. al. (Biochem. Pharmacol., 34, 2967, 1985).
(ii) K+-stimulated ATPase activity.

K+-stimulated ATPase activity was determined at 37° C. in the presence of the following: 10 mM Pipes/-Tris buffer pH 7.0, 2 mM $MgSO_4$, 1 mM KCl, 2 mM $Na_2ATP$ and 3–6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on K+-stimulated ATPase activity.

The effect of the highest concentration of each compound of structure (I) on the recovery of a standard amount of inorganic phosphate was also determined.

RESULTS

The compounds of examples 1 to 3 exhibited $IC_{50}$ values in the range of from 10 to 70μM.

(2) Bone Resorption

Bone resorption was measured by the actions of isolated rat osteoclasts on cortical bone slices (Zaidi et al. Quarterly Journal of Experimental Physiology 1988 73:471–485). Newborn Wistar rats were killed by decapitation and their femora and tibiae removed. Osteoclasts were mechanically disaggregated by curetting the bones into medium followed by agitation with a pipette. Osteoclasts were separated from other cells by sedimentation onto bone slices (15 minutes, 37°) after which the slices were removed and gently washed. The bone slices were then incubated in the presence of test compounds (37°, 10% humidified CO2, 18 hours) and fixed with glutaraldehyde. The degree of bone resorption was then assessed by the area of erosions produced by the osteoclasts using scanning electron microscopy. Data were meaned from measurements of 6 bone slices in each of two independent experiments.

Test compounds were dissolved in ethanol which was also added to control incubations (1%) in the absence of compound.

| | Conc. (μM) | Bone resorption (%) |
|---|---|---|
| Control | | 100 ± 27 |
| Example 2 | 10 | 49 ± 20 |
| | 100 | 0 ± 0 |

Mean ± SEM, n = 12

What is claimed is:

1. A method of inhibiting bone resorption, which comprises administering to a subject in need thereof a compound of structure (I).

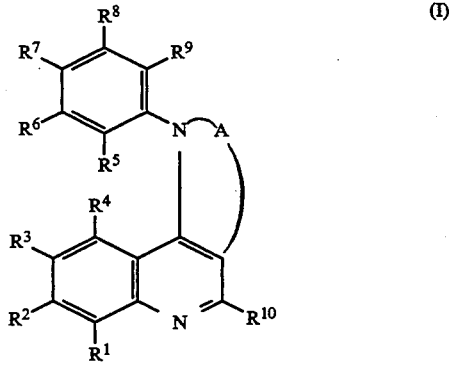

in which
$R^1$ to $R^4$ are the same or different and are each hydrogen, $C_{1-4}$alkyl, $C_{1-6}$alkoxy, phenyl, $C_{1-6}$alkylthio, $C_{1-4}$alkanoyl, amino, $C_{1-6}$alkylamino, di$C_{1-6}$alkylamino, halogen, trifluoromethyl or nitro, provided that at least two of $R^1$ to $R^4$ are hydrogen.
$R^5$ to $R^9$ are the same or different and are each hydrogen, $C_{1-6}$alkyl, $C_{1-6}$alkoxy, $C_{1-6}$alkylthio, halogen, cyano, amino, hydroxy, carbamoyl, carboxy, $C_{1-6}$alkanoyl, trifluoromethyl or nitro, provided that at least two of $R^5$ to $R^9$ are hydrogen;
$R^{10}$ is hydrogen, $C_{1-6}$alkyl, $C_{1-6}$alkoxy, halogen, hydroxy, —$CH_2OH$, $C_{1-6}$alkylthio, $NH(CH_2)_nOH$ in which n is 0 to 4 or a group —$NR^{11}R^{12}$ in which $R^{11}$ and $R^{12}$ are the same or different and are each hydrogen or $C_{1-6}$alkyl or together with the nitrogen atom to which they are attached form a 5-membered saturated or unsaturated ring; and
A is

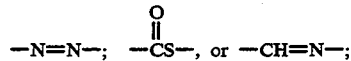

or a pharmaceutically acceptable salt thereof.

2. The method according to claim 1 in which A is —N=N—.

3. The method according to claim 1 wherein structure (I) is 1-(2-methylphenyl)imidazo[4,5-c]quinoline hydrochloride.

4. The method according to claim 1 wherein structure (I) is 1-(2-methylphenyl)triazolo[4,5-c]quinoline.

5. The method according to claim 1 wherein structure (I) is 1-(2-methylphenyl)-2 (3H)-thioimidazo[4,5-c]quinolone.

6. A method of treatment of osteoporosis which comprises administering to a subject in need thereof an effective amount of a compound of formula I as defined in claim 1.